(12) United States Patent
Larkin

(10) Patent No.: US 9,877,705 B2
(45) Date of Patent: Jan. 30, 2018

(54) DEVICE FOR COLLECTING FLUID

(71) Applicant: Daniel Larkin, St. Paul, MN (US)

(72) Inventor: Daniel Larkin, St. Paul, MN (US)

(*) Notice: Subject to any disclaimer, the term of this patent is extended or adjusted under 35 U.S.C. 154(b) by 275 days.

(21) Appl. No.: 14/271,877

(22) Filed: May 7, 2014

(65) Prior Publication Data

US 2015/0320403 A1 Nov. 12, 2015

(51) Int. Cl.
*A61B 5/00* (2006.01)
*A61B 10/00* (2006.01)

(52) U.S. Cl.
CPC .................. *A61B 10/007* (2013.01)

(58) Field of Classification Search
CPC .... A61B 10/007; A61B 10/045; A61B 5/1405
USPC ........................................................ 600/573
See application file for complete search history.

(56) References Cited

U.S. PATENT DOCUMENTS

| 2,433,538 | A | * | 12/1947 | Warner | .............. | A61B 10/0058 |
| | | | | | | 600/573 |
| 4,320,752 | A | * | 3/1982 | Comparetto | .............. | A61F 6/04 |
| | | | | | | 128/844 |
| 5,318,042 | A | | 6/1994 | Gray | | |
| 5,579,784 | A | | 12/1996 | Harari | | |
| 5,823,191 | A | | 10/1998 | Cho | | |
| 6,098,625 | A | * | 8/2000 | Winkler | .................... | A61F 6/04 |
| | | | | | | 128/842 |
| 6,672,309 | B1 | | 6/2004 | Al-Salem | | |

* cited by examiner

*Primary Examiner* — Daniel Cerioni
(74) *Attorney, Agent, or Firm* — Dicke, Billig & Czaja, PLLC

(57) ABSTRACT

A device for collecting fluid from a penis includes a fluid collection structure configured to be attached to a glans of the penis directly over a meatus of the penis such that a substantial majority of the glans remains uncovered by the device. The device includes an attachment structure configured to secure the fluid collection structure to the penis.

18 Claims, 5 Drawing Sheets

DEVICE FOR COLLECTING FLUID

BACKGROUND

Current techniques for collecting a urine specimen from a male patient typically involve the use of a large bag device that covers the entire penis. Such devices tend to be large, bulky, and uncomfortable.

SUMMARY

One embodiment is directed to a device for collecting fluid from a penis. The device includes a fluid collection structure configured to be attached to a glans of the penis directly over a meatus of the penis such that a substantial majority of the glans remains uncovered by the device. The device includes an attachment structure configured to secure the fluid collection structure to the penis.

DETAILED DESCRIPTION

Figure 1:
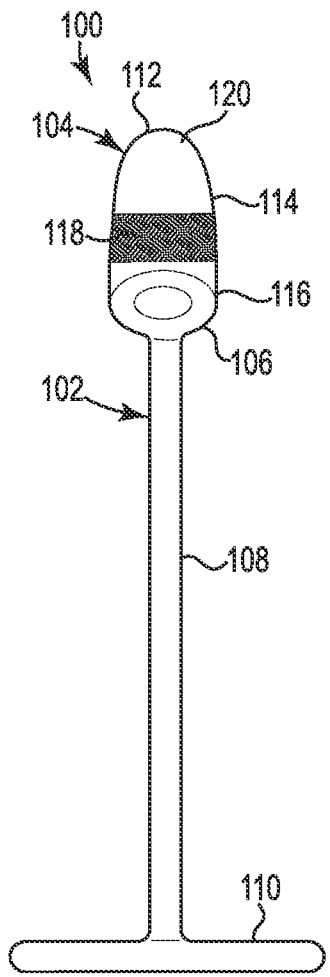
FIG. 1 is a diagram illustrating a front view of a fluid collection device according to one embodiment.
Figure 2:
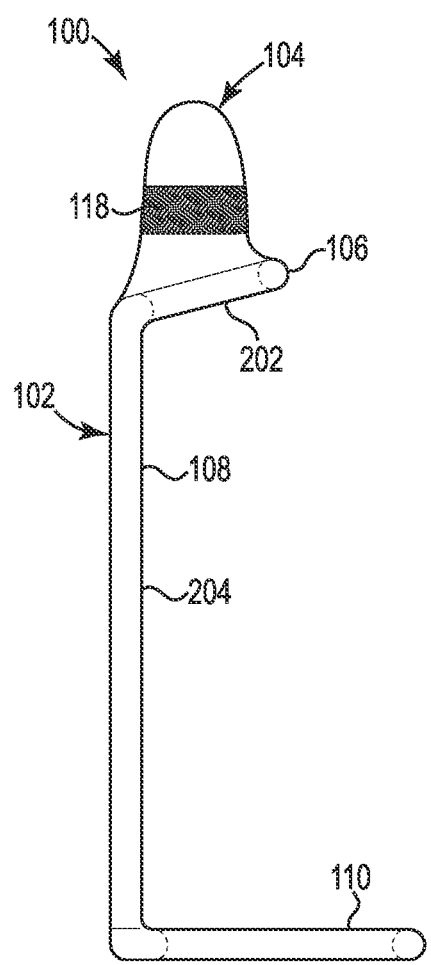
FIG. 2 is a diagram illustrating a side view of the fluid collection device shown in FIG. 1 according to one embodiment.

FIG. 1 is a diagram illustrating a front view of a fluid collection device 100 according to one embodiment. FIG. 2 is a diagram illustrating a side view of the fluid collection device 100 shown in FIG. 1 according to one embodiment. Device 100 is configured to collect urine samples and function as a more comfortable incontinence device than previous devices. Device 100 may also be used as a condom-like device to collect semen during sexual intercourse.

Device 100 includes an attachment structure 102 and a fluid collection structure 104. The attachment structure 102 includes a distal band 106, an arm 108, and a proximal elastic ring 110. The arm 108 is coupled to the distal band 106 and the proximal ring 110, and interconnects the band 106 and the ring 110. Fluid collection structure 104 is coupled to the distal band 106. Fluid collection structure 104 comprises a substantially tubular body 114 with an open end 116 and a closed end 112. The open end 116 is connected and fluidly sealed to the distal band 106, such that the distal band 106 encircles the open end 116. In one embodiment, device 100 has an overall length of about 5 cm to 7 cm.

In one embodiment, the open end 116 of the tubular body 114 has a diameter of between about 3 mm to 6 mm, and the tubular body 114 has a length from the open end 116 to the closed end 112 of about 5 mm to 1.2 cm. In one embodiment, the distal band 106 is substantially circular and has an inner diameter of between about 3 mm and 6 mm, and an outer diameter of between about 4 mm and 1 cm. In another embodiment, distal band 106 has an elliptical shape. Distal band 106 includes an adhesive covered surface 202.

Arm 108 according to one embodiment has a length of about 3 cm to about 7 cm, and a width of about 2 mm to 4 mm. Arm 108 includes an adhesive covered surface 204, which extends along the entire length of the arm 108 in one embodiment. Proximal ring 110 according to one embodiment has a diameter of about 3 cm.

In one embodiment, an absorption fabric 118 is removably secured (e.g., with an adhesive) within the tubular body 114. In one implementation, device 100 is made entirely from latex, with the exception of fabric 118, which is cotton in one embodiment. The fabric 118 draws fluid away from the skin of the penis and into a distal tip 120 of the tubular body 114. The fabric 118 promotes less irritation of any skin contacting the distal band 106. The fabric 118 also helps to prevent contamination of the fluid sample by skin bacteria by absorbing and holding onto a quantity of the fluid and keeping it away from the skin of the penis, and may be used as a culture starter for sampling urine for culture. Other embodiments may not include the fabric 118.

Figure 3:
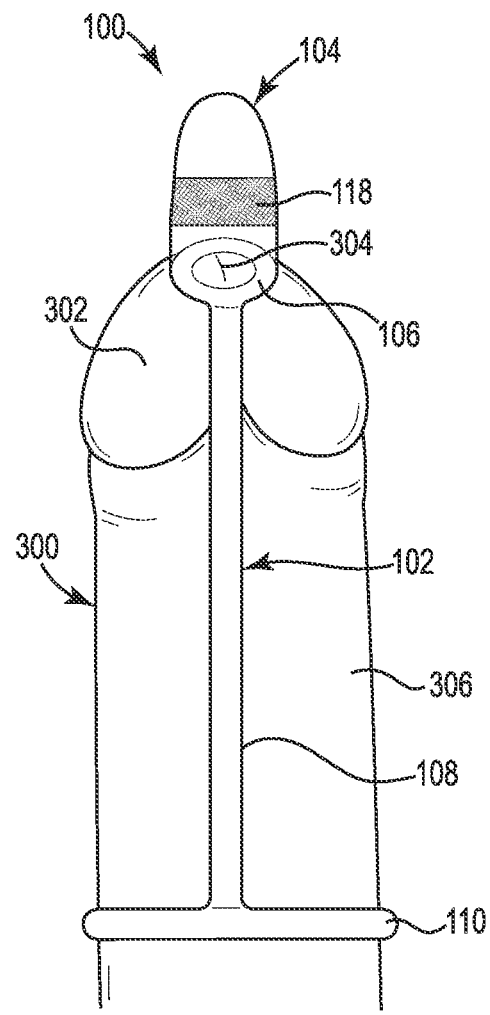
FIG. 3 is a diagram illustrating the fluid collection device shown in FIGS. 1 and 2 applied to a penis according to one embodiment.

FIG. 3 is a diagram illustrating the fluid collection device 100 shown in FIGS. 1 and 2 applied to a penis 300 according to one embodiment. The adhesive covered surface 202 of the distal band 106 is configured to be adhesively attached to and fluidly sealed against the glans or head 302 of penis 300 directly over the meatus or natural opening 304 of the penis 300. After attachment, the distal band 106 encircles the meatus 304, leaving a substantial majority of the glans 302 and shaft 306 uncovered or exposed.

In one embodiment, arm 108 is a narrow strip, and the adhesive covered surface 204 of the arm 108 extends along the length of the arm 108 and is configured to be adhesively attached to an underside (ventral side) of the glans 302 and shaft 306 of the penis 300. In one embodiment, proximal elastic ring 110 is formed from latex or another stretchy or elastic material, and is similar to the elastic rings typically found on the open end of many conventional condoms. In one embodiment, proximal elastic ring 110 has a circular cross-sectional shape. In another embodiment, proximal elastic ring 110 has a substantially flat cross-sectional shape. The elastic nature of the proximal ring 110 accommodates penis shafts of various diameters, and allows the ring 110 to be comfortably and securely attached around the shaft 306 of a penis 300. Proximal elastic ring 110 is configured to be rolled over the glans 302 and along the shaft 306 of the penis 300 in the same manner as a condom is typically applied. Arm 108 is initially wrapped around the proximal ring 110 such that it becomes unwrapped from the proximal ring 110 as the proximal ring is rolled onto the penis 300.

In one embodiment, the adhesive surfaces 202 and 204 are initially covered by one or more removable strips. Fluid collection structure 104 is held by a user over the meatus 304 while the user rolls the proximal ring 110 onto the shaft 306 of the penis 300. After the proximal ring 110 is rolled onto the shaft of the penis 300, the removable strips are removed to expose the adhesive surfaces, and the distal band 106 and the arm 108 are adhesively secured to the penis 300 via the adhesive surfaces 202 and 204. When device 100 is used as a condom, the glans 302 remains substantially uncovered by the attached device 100 and is free to contact the vaginal tissue, and ejaculate is collected by the fluid collection structure 104.

Figure 4:
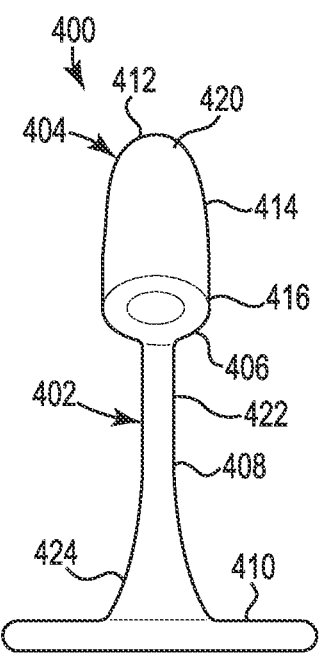
FIG. 4 is a diagram illustrating a front view of a fluid collection device according to another embodiment.

FIG. 4 is a diagram illustrating a front view of a fluid collection device 400 according to another embodiment. Device 400 is configured to collect urine samples and function as a more comfortable incontinence device than previous devices. Device 400 may also be used as a condom-like device to collect semen during sexual intercourse.

Device 400 includes an attachment structure 402 and a fluid collection structure 404. The attachment structure 402 includes a distal band 406, an arm 408, and a proximal elastic ring 410. The arm 408 is coupled to the distal band 406 and the proximal ring 410, and interconnects the band 406 and the ring 410. Fluid collection structure 404 is coupled to the distal band 406. Fluid collection structure 404 comprises a substantially tubular body 414 with an open end 416 and a closed end 412. The open end 416 is connected and fluidly sealed to the distal band 406, such that the distal band 406 encircles the open end 416. In one embodiment, the materials, dimensions, and functionality of device 400 are the same as those described above for device 100, with the exception of the arm 408, which includes a flared portion 424 in the embodiment shown in FIG. 4, and device 400 does not include an absorbent fabric 118 in the fluid collection structure 404 in the illustrated embodiment. It is noted that, in other embodiments, device 100 may be provided with a flared portion 424, and device 400 may be provided with an absorbent fabric 118.

As shown in FIG. 4, arm 408 includes a first portion 422 that is connected to the band 406 and extends away from the band 406. The first portion 422 has a substantially constant width along the length of this portion 422, which is about 2 mm to 4 mm in one embodiment. In the illustrated embodiment, the first portion 422 has a length that is equal to about half of the overall length of the arm 408. The flared portion 424 extends away from the first portion 422 and toward the ring 410. The flared portion 424 has a width that gradually increases along the length of the flared portion 424, with the widest end of the flared portion 424 being connected to the ring 410. In one embodiment, the width of the flared portion gradually increases from about 2 mm to 4 mm at one end to about 6 mm to 1.2 cm at the second end. In the illustrated embodiment, the flared portion 424 has a length that is equal to about half of the overall length of the arm 408. The flared portion 424 provides the attachment structure 402 with additional structural support.

The distal band 406 is configured to be adhesively attached to and fluidly sealed against the glans or head of a penis directly over the meatus or natural opening of the penis. After attachment, the distal band 406 encircles the meatus, leaving a substantial majority of the glans and shaft uncovered or exposed.

The arm 408 is configured to be adhesively attached to an underside (ventral side) of the glans and shaft of the penis. Proximal elastic ring 410 is configured to be rolled over the glans and along the shaft of the penis in the same manner as a condom is typically applied. Arm 408 is initially wrapped around the proximal ring 410 such that it becomes unwrapped from the proximal ring 410 as the proximal ring is rolled onto the penis.

In one embodiment, the device 400 includes adhesive surfaces that are initially covered by one or more removable strips. Fluid collection structure 404 is held by a user over the meatus while the user rolls the proximal ring 410 onto the shaft of the penis. After the proximal ring 410 is rolled onto the shaft of the penis, the removable strips are removed to expose the adhesive surfaces, and the attachment structure 402 and the fluid collection structure 404 are adhesively secured to the penis via the adhesive surfaces. When device 400 is used as a condom, the glans remains substantially uncovered by the attached device 400 and is free to contact the vaginal tissue, and ejaculate is collected by the fluid collection structure 404.

Figure 5:
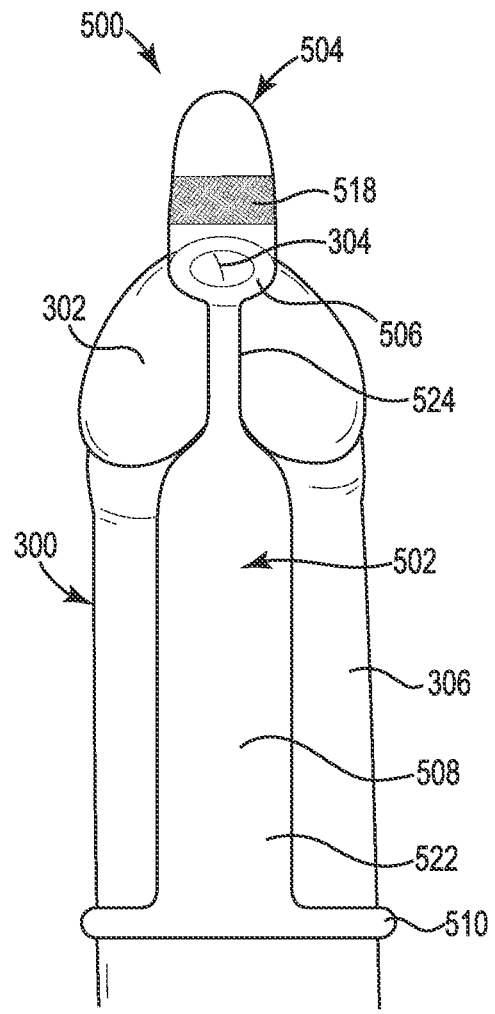
FIG. 5 is a diagram illustrating a fluid collection device applied to a penis according to another embodiment.

FIG. 5 is a diagram illustrating a fluid collection device 500 applied to a penis 300 according to another embodiment. Device 500 is configured to collect urine samples and function as a more comfortable incontinence device than previous devices. Device 500 may also be used as a condom-like device to collect semen during sexual intercourse.

Device 500 includes an attachment structure 502 and a fluid collection structure 504. The attachment structure 502 includes a distal band 506, an arm 508, and a proximal elastic ring 510. The arm 508 is coupled to the distal band 506 and the proximal ring 510, and interconnects the band 506 and the ring 510. Fluid collection structure 504 is coupled to the distal band 506. Fluid collection structure 504 comprises a substantially tubular body with an open end and a closed end. The open end is connected and fluidly sealed to the distal band 506, such that the distal band 506 encircles the open end. In one embodiment, device 500 has an overall length of about 5 cm to 7 cm.

In one embodiment, the open end of the fluid collection structure 504 has a diameter of between about 3 mm to 6 mm, and the fluid collection structure 504 has a length from the open end to the closed end of about 5 mm to 1.2 cm. In one embodiment, the distal band 506 is substantially circular and has an inner diameter of between about 3 mm and 6 mm, and an outer diameter of between about 4 mm and 1 cm. In another embodiment, distal band 506 has an elliptical shape. Proximal ring 510 according to one embodiment has a diameter of about 3 cm.

Arm 508 according to one embodiment has a length of about 3 cm to about 7 cm. Arm 508 includes a first portion 522 that is connected to the proximal ring 510 and extends away from the ring 610. The first portion 522 has a substantially constant width along the length of this portion 522, which is about 6 mm to 12 mm in one embodiment. In the illustrated embodiment, the first portion 522 has a length that is equal to about three fourths of the overall length of the arm 508. The first portion 522 tapers into a narrower second portion 524, which extends away from the first portion 522 and toward the distal band 506. The second portion 524 has a substantially constant width along the length of this portion 524, which is about 2 mm to 4 mm in one embodiment. In the illustrated embodiment, the second portion 524 has a length that is equal to about one fourth of the overall length of the arm 508. The first portion 522 provides the attachment structure 502 with additional structural support.

In one embodiment, an absorption fabric 518 is removably secured (e.g., with an adhesive) within the fluid collection structure 504. In one implementation, device 500 is made entirely from latex, with the exception of fabric 518, which is cotton in one embodiment. The fabric 518 draws fluid away from the skin of the penis and into a distal tip of the fluid collection structure 504. The fabric 518 promotes less irritation of any skin contacting the distal band 506. The fabric 518 also helps to prevent contamination of the fluid sample by skin bacteria by absorbing and holding onto a quantity of the fluid and keeping it away from the skin of the penis, and may be used as a culture starter for sampling urine for culture. Other embodiments may not include the fabric 518.

An adhesive covered surface of the distal band 506 is configured to be adhesively attached to and fluidly sealed against the glans or head 302 of penis 300 directly over the meatus or natural opening 304 of the penis 300. After attachment, the distal band 506 encircles the meatus 304, leaving a substantial majority of the glans 302 and shaft 306 uncovered or exposed.

In one embodiment, arm 508 includes an adhesive covered surface that extends along the length of the arm 508 and is configured to be adhesively attached to an underside (ventral side) of the glans 302 and shaft 306 of the penis 300. In one embodiment, proximal elastic ring 510 is formed from latex or another stretchy or elastic material, and is similar to the elastic rings typically found on the open end of many conventional condoms. In one embodiment, proximal elastic ring 510 has a circular cross-sectional shape. In another embodiment, proximal elastic ring 510 has a substantially flat cross-sectional shape. The elastic nature of the proximal ring 510 accommodates penis shafts of various diameters, and allows the ring 510 to be comfortably and securely attached around the shaft 306 of a penis 300. Proximal elastic ring 510 is configured to be rolled over the glans 302 and along the shaft 306 of the penis 300 in the same manner as a condom is typically applied. Arm 508 is initially wrapped around the proximal ring 510 such that it becomes unwrapped from the proximal ring 510 as the proximal ring is rolled onto the penis 300.

In one embodiment, the adhesive surfaces of device 500 are initially covered by one or more removable strips. Fluid collection structure 504 is held by a user over the meatus 304 while the user rolls the proximal ring 510 onto the shaft 306 of the penis 300. After the proximal ring 510 is rolled onto the shaft of the penis 300, the removable strips are removed to expose the adhesive surfaces, and the distal band 506 and the arm 508 are adhesively secured to the penis 300 via the adhesive surfaces. When device 500 is used as a condom, the glans 302 remains substantially uncovered by the attached device 500 and is free to contact the vaginal tissue, and ejaculate is collected by the fluid collection structure 504.

Figure 6:
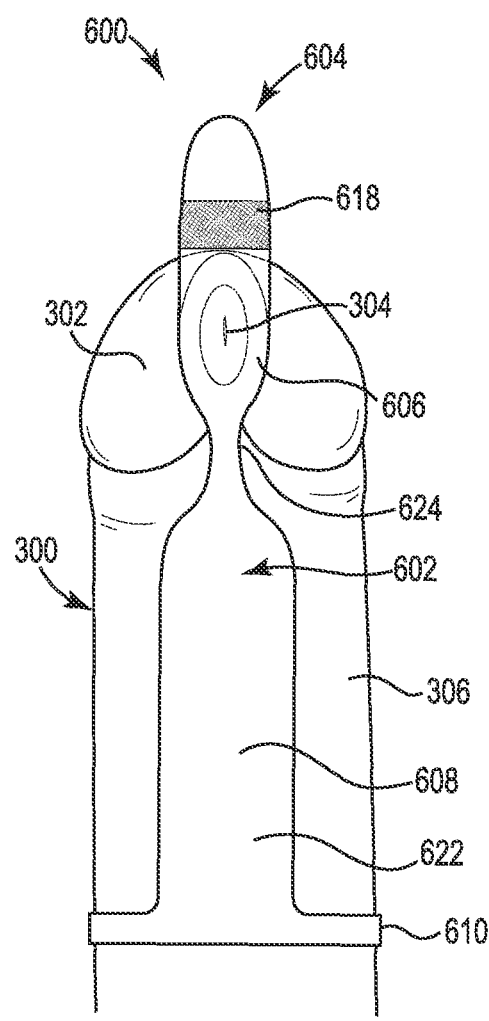
FIG. 6 is a diagram illustrating a fluid collection device applied to a penis according to yet another embodiment.

FIG. 6 is a diagram illustrating a fluid collection device 600 applied to a penis 300 according to yet another embodiment. Device 600 is configured to collect urine samples and function as a more comfortable incontinence device than previous devices. Device 600 may also be used as a condom-like device to collect semen during sexual intercourse.

Device 600 includes an attachment structure 602 and a fluid collection structure 604. The attachment structure 602 includes a distal band 606, an arm 608, and a proximal elastic ring 610. The arm 608 is coupled to the distal band 606 and the proximal ring 610, and interconnects the band 606 and the ring 610. Fluid collection structure 604 is coupled to the distal band 606. Fluid collection structure 604 comprises a substantially tubular body with an open end and a closed end. The open end is connected and fluidly sealed to the distal band 606, such that the distal band 606 encircles the open end. In one embodiment, device 600 has an overall length of about 5 cm to 7 cm.

In one embodiment, the open end of the fluid collection structure 604 has an elliptical shape and has a diameter along a minor axis of between about 3 mm to 6 mm and a diameter along a major axis of between about 6 mm to about 12 mm, and the fluid collection structure 604 has a length from the open end to the closed end of about 5 mm to 1.2 cm. In one embodiment, the distal band 606 has an elliptical shape and has an inner diameter along a minor axis of between about 3 mm and 6 mm, and an outer diameter along the minor axis of between about 4 mm and 1 cm. The distal band 606 according to one embodiment has an inner diameter along a major axis of between about 6 mm and 12 mm, and an outer diameter along the major axis of between about 8 mm and 1.5 cm. In another embodiment, distal band 606 has a circular shape. Proximal ring 610 according to one embodiment has a diameter of about 3 cm.

Arm 608 according to one embodiment has a length of about 3 cm to about 7 cm. Arm 608 includes a first portion 622 that is connected to the proximal ring 610 and extends away from the ring 610. The first portion 622 has a substantially constant width along the length of this portion 622, which is about 6 mm to 12 mm in one embodiment. In the illustrated embodiment, the first portion 622 has a length that is equal to about three fourths of the overall length of the arm 608. The first portion 622 tapers into a narrower second portion 624, which extends away from the first portion 622 and toward the distal band 606. The second portion 624 has a substantially constant width along the length of this portion 624, which is about 3 mm to 5 mm in one embodiment. In the illustrated embodiment, the second portion 624 has a length that is equal to about one fourth of the overall length of the arm 608. The first portion 622 provides the attachment structure 602 with additional structural support.

In one embodiment, an absorption fabric 618 is removably secured (e.g., with an adhesive) within the fluid collection structure 604. In one implementation, device 600 is made entirely from latex, with the exception of fabric 618, which is cotton in one embodiment. The fabric 618 draws fluid away from the skin of the penis and into a distal tip of the fluid collection structure 604. The fabric 618 promotes less irritation of any skin contacting the distal band 606. The fabric 618 also helps to prevent contamination of the fluid sample by skin bacteria by absorbing and holding onto a quantity of the fluid and keeping it away from the skin of the penis, and may be used as a culture starter for sampling urine for culture. Other embodiments may not include the fabric 618.

An adhesive covered surface of the distal band 606 is configured to be adhesively attached to and fluidly sealed against the glans or head 302 of penis 300 directly over the meatus or natural opening 304 of the penis 300. After attachment, the distal band 606 encircles the meatus 304, leaving a substantial majority of the glans 302 and shaft 306 uncovered or exposed.

In one embodiment, arm 608 includes an adhesive covered surface that extends along the length of the arm 608 and is configured to be adhesively attached to an underside (ventral side) of the glans 302 and shaft 306 of the penis 300. In one embodiment, proximal elastic ring 610 is formed from latex or another stretchy or elastic material, and is similar to the elastic rings typically found on the open end of many conventional condoms. In one embodiment, proximal elastic ring 610 has a circular cross-sectional shape. In another embodiment, proximal elastic ring 610 has a substantially flat cross-sectional shape. The elastic nature of the proximal ring 610 accommodates penis shafts of various diameters, and allows the ring 610 to be comfortably and securely attached around the shaft 306 of a penis 300. Proximal elastic ring 610 is configured to be rolled over the glans 302 and along the shaft 306 of the penis 300 in the same manner as a condom is typically applied. Arm 608 is initially wrapped around the proximal ring 610 such that it becomes unwrapped from the proximal ring 610 as the proximal ring is rolled onto the penis 300.

In one embodiment, the adhesive surfaces of device 600 are initially covered by one or more removable strips. Fluid collection structure 604 is held by a user over the meatus 304 while the user rolls the proximal ring 610 onto the shaft 306 of the penis 300. After the proximal ring 610 is rolled onto the shaft of the penis 300, the removable strips are removed to expose the adhesive surfaces, and the distal band 606 and the arm 608 are adhesively secured to the penis 300 via the adhesive surfaces. When device 600 is used as a condom, the glans 302 remains substantially uncovered by the attached device 600 and is free to contact the vaginal tissue, and ejaculate is collected by the fluid collection structure 604.

Figure 7:
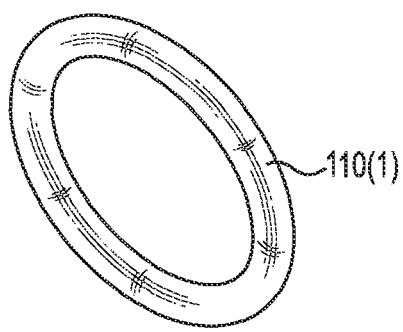
FIG. 7 is a diagram illustrating a perspective view of a proximal ring of a fluid collection device according to one embodiment.

FIG. 7 is a diagram illustrating a proximal ring 110(1) of a fluid collection device according to one embodiment. Proximal ring 110(1) may be used as the proximal ring for any of the fluid collection devices 100, 400, 500, and 600. The proximal ring 110(1) has a circular cross-sectional shape, and has a thickness of about 1 mm (i.e., the diameter of the circular cross-section is about 1 mm).

Figure 8:
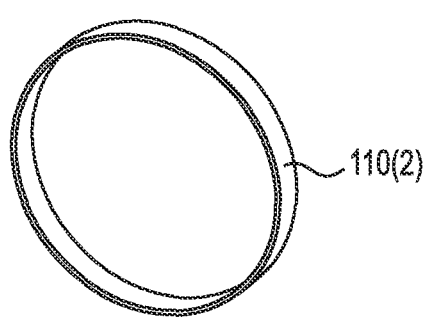
FIG. 8 is a diagram illustrating a perspective view of a proximal ring of a fluid collection device according to another embodiment.

FIG. 8 is a diagram illustrating a proximal ring 110(2) of a fluid collection device according to another embodiment. Proximal ring 110(2) may be used as the proximal ring for any of the fluid collection devices 100, 400, 500, and 600. The proximal ring 110(2) has a flat cross-sectional shape, such as a rectangular shape or elliptical shape, and has a lateral width of about 1 mm and a thickness of less than about 0.5 mm. The flat cross-sectional shape of the proximal ring 110(2) allows the ring 110(2) to sit almost flush against the skin, which helps prevent the ring 110(2) from sliding down when the fluid collection device is used as a condom type device.

One embodiment is directed to a device for collecting fluid from a penis. The device includes a fluid collection structure configured to be attached to a glans of the penis directly over a meatus of the penis such that a substantial majority of the glans remains uncovered by the device. The device also includes an attachment structure configured to secure the fluid collection structure to the penis.

In one form of this embodiment, the attachment structure comprises an elastic ring configured to be rolled onto a shaft of the penis, and an arm that interconnects the elastic ring and the fluid collection structure. The arm according to one embodiment comprises an adhesive covered surface extending along a length of the arm that is configured to be attached to a shaft of the penis. In one embodiment, the arm has a length of about 3 cm to about 7 cm, and a width of about 2 mm to 4 mm. In one embodiment, the arm includes a flared portion, and a widest end of the flared portion is connected to the elastic ring. The arm according to one embodiment includes a first portion having a substantially constant width along a length of the first portion, and the first portion is connected to the elastic ring and tapers to a second portion having a substantially constant width along the length of the second portion. The attachment structure according to one embodiment includes a band connected to the arm and the fluid collection structure. In one embodiment, the fluid collection structure comprises a substantially tubular body with an open end and a closed end, and wherein the open end is fluidly sealed to the band. The band according to one embodiment includes an adhesive covered surface configured to be attached to the glans of the penis directly over the meatus. In one embodiment, the tubular body has a diameter of between about 3 mm and 6 mm, and has a length of about 5 mm to about 1.2 cm. In one embodiment, the device also comprises an absorption fabric secured within the fluid collection structure. The absorption fabric is configured to draw fluid away from the penis and into a distal tip of the fluid collection structure.

Another embodiment is directed to a device for collecting fluid from a penis, and includes a fluid collection structure configured to be adhesively attached to a glans of the penis directly over a meatus of the penis such that a substantial majority of the glans remains uncovered by the device. The device includes an elastic ring configured to be rolled onto a shaft of the penis, and an arm that interconnects the elastic ring and the fluid collection structure, and that is configured to be adhesively attached to the penis.

The dimensions of devices 100, 400, 500, and 600 may vary from those given above. For example, a pediatric version of the device may be smaller than an adult version of the device.

What is claimed is:

1. A device for collecting fluid from a penis, the device comprising:
    a fluid collection structure configured to be attached to a glans of the penis directly over a meatus of the penis such that a majority of the glans remains uncovered by the device; and
    an attachment structure configured to secure the fluid collection structure to the penis, wherein the attachment structure comprises an elastic ring configured to be rolled onto a shaft of the penis, a band connected to the fluid collection structure, and only a single arm that interconnects the elastic ring and the band.

2. The device of claim 1, wherein the arm comprises an adhesive covered surface extending along a length of the arm that is configured to be attached to a shaft of the penis.

3. The device of claim 1, wherein the arm has a length of 3 cm to 7 cm, and a width of 2 mm to 4 mm.

4. The device of claim 1, wherein the arm includes a flared portion.

5. The device of claim 4, wherein a widest end of the flared portion is connected to the elastic ring.

6. The device of claim 1, wherein the arm includes a first portion having a constant width along a length of the first portion, and wherein the first portion is connected to the elastic ring and tapers to a second portion having a constant width along the length of the second portion.

7. The device of claim 1, wherein the fluid collection structure comprises a tubular body with an open end and a closed end, and wherein the open end is fluidly sealed to the band.

8. The device of claim 7, wherein the band includes an adhesive covered surface configured to be attached to the glans of the penis directly over the meatus.

9. The device of claim 7, wherein the tubular body has a diameter of between 3 mm and 6 mm.

10. The device of claim 9, wherein the tubular body has a length of 5 mm to 1.2 cm.

11. The device of claim 1, and further comprising an absorption fabric secured within the fluid collection structure.

12. The device of claim 11, wherein the absorption fabric is configured to draw fluid away from the penis and into a distal tip of the fluid collection structure.

13. A device for collecting fluid from a penis, the device comprising:
    a fluid collection structure configured to be adhesively attached to a glans of the penis directly over a meatus of the penis such that a majority of the glans remains uncovered by the device;
    an elastic ring configured to be rolled onto a shaft of the penis;
    an interconnection arm that interconnects the elastic ring and the fluid collection structure, and that is configured to be adhesively attached to the penis, wherein the interconnection arm that interconnects the elastic ring and the fluid collection structure has a length of at least 3 cm;
    a band connected to the fluid collection structure; and wherein the interconnection arm is a single interconnection arm that interconnects the elastic ring and the band, and wherein the elastic ring and the band are interconnected only by the single interconnection arm.

14. The device of claim 13, wherein the interconnection arm has a length of 3 cm to 7 cm, and a width of 2 mm to 4 mm.

15. The device of claim 13, wherein the fluid collection structure comprises a tubular body with an open end and a closed end, and wherein the open end is configured to be fluidly sealed to the glans.

16. The device of claim 15, wherein the tubular body has a diameter of between 3 mm and 6 mm.

17. The device of claim 16, wherein the tubular body has a length of 5 mm to 1.2 cm.

18. The device of claim 13, and further comprising an absorption fabric secured within the fluid collection structure, wherein the absorption fabric is configured to draw fluid away from the penis and into a distal tip of the fluid collection structure.

* * * * *